United States Patent [19]

Puetter et al.

[11] Patent Number: 4,802,965

[45] Date of Patent: Feb. 7, 1989

[54] CONCENTRATING AQUEOUS SOLUTIONS OF ORGANIC COMPOUNDS WHICH CONTAIN SALTS, WITH SIMULTANEOUS REDUCTION OF THE SALT CONTENT

[75] Inventors: Hermann Puetter, Neustadt; Eckhard Roske, Ludwigshafen, both of Fed. Rep. of Germany

[73] Assignee: BASF Aktiengesellschaft, Ludwigshafen, Fed. Rep. of Germany

[21] Appl. No.: 809,582

[22] Filed: Dec. 16, 1985

[30] Foreign Application Priority Data

Dec. 21, 1984 [DE] Fed. Rep. of Germany ....... 3446695

[51] Int. Cl.[4] ............................................. B01D 13/02
[52] U.S. Cl. .................................. 204/182.4; 204/301
[58] Field of Search .................... 204/182.4, 182.5, 301

[56] References Cited

U.S. PATENT DOCUMENTS

| | | | |
|---|---|---|---|
| 2,827,428 | 3/1958 | Noble | 204/182.4 |
| 2,848,403 | 8/1958 | Rosenberg | 204/182.4 |
| 2,860,091 | 11/1958 | Rosenberg | 204/182.4 X |
| 3,136,710 | 6/1964 | Duboy | 204/182.4 |
| 3,383,245 | 5/1968 | Scallet et al. | 204/182.4 X |
| 3,437,580 | 4/1969 | Arrance et al. | 204/182.4 X |
| 3,525,682 | 8/1970 | McRae et al. | 204/182.4 X |
| 3,718,560 | 2/1973 | Sugiyama et al. | 204/182.4 |
| 4,608,141 | 8/1986 | Chlanda et al. | 204/182.5 |
| 4,613,416 | 9/1986 | Kau et al. | 204/182.4 |

FOREIGN PATENT DOCUMENTS

597825  5/1960  Canada ............................ 204/182.4

OTHER PUBLICATIONS

Chemistry & Industry, (Jan. 4, 1958), pp. 8–12.
D. S. Flett, Ion Exchange Membranes, Ellis Horwood, Chinchester 1983, pp. 179–191.

Primary Examiner—John F. Niebling
Assistant Examiner—John S. Starsiak, Jr.
Attorney, Agent, or Firm—John H. Shurtleff

[57] ABSTRACT

Aqueous solutions of organic compounds which contain salts are concentrated by electrodialysis with simultaneous reduction of the salt content of these solutions, the concentrate used being an aqueous salt solution which is not less than 1 molar.

16 Claims, 1 Drawing Sheet

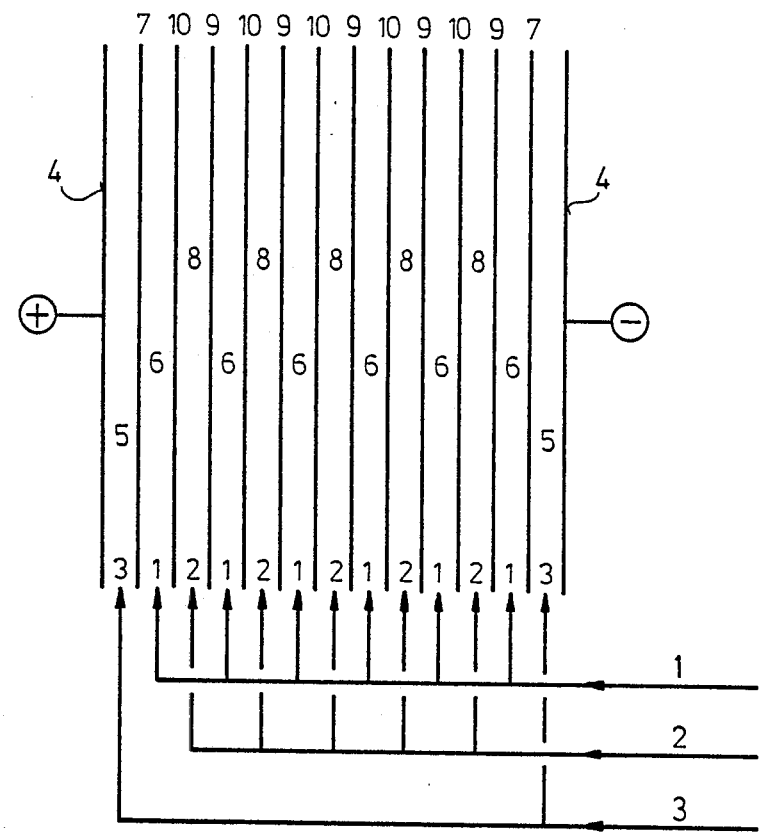

CONCENTRATING AQUEOUS SOLUTIONS OF ORGANIC COMPOUNDS WHICH CONTAIN SALTS, WITH SIMULTANEOUS REDUCTION OF THE SALT CONTENT

The present invention relates to a process for concentrating aqueous solutions of organic compounds which contain salts, with simultaneous reduction of the salt content of these solutions by electrodialysis.

The production of aqueous solutions of organic compounds which have a low salt content is very important industrially. The salt content of aqueous solutions of organic compounds is frequently reduced using membrane methods, such as ultrafiltration or reverse osmosis. Ultrafiltration permits the simultaneous removal of solvents and low molecular weight salts from organic compounds, but is restricted to high molecular weight products. It displays its optimum separating properties in the macromolecular range (particle size greater than $10^{-2} \mu m$), whereas organic compounds having a molecular weight of about $10^3$ or less (particle size less than $10^{-3} \mu m$) cannot be separated from salts by ultrafiltration.

Reverse osmosis permits the concentration of solutions of organic compounds by removal of solvents, in particular water. However, it is not in general capable of separating salts from other substances, so that troublesome ionic impurities accumulate during concentration of the desired product.

There has been no lack of attempts to develop methods occupying a position at the boundary between ultrafiltration and reverse osmosis, in order to separate organic compounds from salts. Although these methods achieve a certain degree of concentration, they are generally limited to molecules having a molecular weight >1000, in general >5000. Another difficulty is the fact that there is no sharp separation limit. For example, even with the best membranes, it is only possible to separate from one another substances with molecular weights that differ by a factor of 2 or more.

Electrodialyis has also been used for separating salts from aqueous solutions, for example for the desalination of brackish water and for the production of table salt. The aim is the same in both cases: to separate off salt (NaCl) with very little transport of water. Hence, all modern ion exchange membranes are also optimized for good performance in this respect. To increase the current efficiency and desalination rate in electrodialysis, large differences between the concentration of the diluate and that of the concentrate are avoided since the salt content of the diluate cannot be reduced below a limiting value of about 0.1% in the case of high salt contents of the concentrate, owing to back diffusion. Where the salt concentration of the concentrate is high (>1 M) the perm selectivity of the membrane breaks down; in dilute solutions, it is 85–95%.

Electrodialysis is described, for example, by H. Strathmann in Trennung von molekularen Mischungen mit Hilfe synthetischer Membranen, Steinkopf, Darmstadt, 1979, pages 76–86, and by D.S. Flett in Ion Exchange Membranes, Ellis Horwood, Chichester 1983, pages 179–191.

We have found that aqueous solutions of organic compounds which contain salts can be concentrated with simultaneous reduction of the salt content if the salt-containing aqueous solution of the organic compound is subjected to electrodialysis, and an aqueous salt solution which is not less than 1 molar is used as the concentrate.

Starting solutions for the novel process are aqueous solutions of colorless or colored organic compounds which contain, as impurities, salts or the free acids from which these salts are derived. The solutions may contain a very wide variety of water-soluble organic compounds, for example ionic compounds, such as organic acids, eg. carboxylic acids, sulfonic acids or phosphonic acids, metal complexes, heterocylic compounds, ammonium compounds, such as quaternary compounds, phosphonium salts, betaines, such as aminocarboxylic acids, aminosulfonic acids or heterocyclic betaines, or electrically neutral organic compounds, such as carbohydrates, ethers, nitriles, amines, azo compounds, heterocyclic compounds or water-soluble oligomers or polymers.

The lower molecular weight limit down to which it is possible to separate the organic compounds from the salts depends on whether the compounds are electrically neutral or ionic. This limit is about 60 in the case of neutral substances, and about 120 in the case of ionic substances. Although it is also possible to achieve separation effects below these values, fairly large losses of the organic compound must be expected. There is no upper limit to the molecular weight of the organic compound, provided that it has a certain watersolubility. In the case of ionic monomeric organic compounds, a molecular weight of from 200 to 2000 is preferred. It is also possible to use, for example, water-soluble oligomers or polymers having molecular weights of from 2000 to 2 million.

The aqueous solutions of the organic compounds contain as salts, for example, alkali metal, alkaline earth metal or ammonium halides, nitrates, sulfates, carbonates, sulfides, sulfites, formates, acetates or phosphates, or water-soluble salts of heavy metals, such as copper, zinc, silver, tin or iron. In the process according to the invention, any content of the free acids from which these salts are derived, eg. hydrochloric acid, sulfuric acid, carbonic acid, acetic acid, formic acid, nitric acid or phosphoric acid, is also reduced.

For the novel process, it is possible to use aqueous solutions which, for example, contain not more than 50% by weight of the organic compound and have a salt content of not more than 30% by weight.

The concentrate used for the novel process is an aqueous salt solution which is not less than 1 molar. Examples of suitable salts are water-soluble halides, sulfides, sulfites, sulfates, carbonates, formates or acetates, preferably those of ammonium or of the alkali or alkaline earth metals. For example, NaCL, KCl, LiCl, NH4CL, Na2SO4, Li2SO4 and K2SO4 are particularly sui the sulfates being preferred. In particular, an aqueous solution of the chlorides or bromides of the alkali metals which is not less than 3 molar, or a solution of the stated salts which is saturated at room temperature, is employed.

Electrodialysis is carried out in a conventional manner in an electrodialysis apparatus as used, for example, for the desalination of brackish water, fruit juices and whey and is effected at not more than 100° C., preferably from 15° to 80° C. The current density is from 10 to 0.01, preferably from 5 to 0.05, A/dm$^2$. The cell voltage is from 0.5 to 2 V per subcell, the latter consisting of a diluate Chamber and a concentrate chamber.

In the novel process, substantial concentration of salt-containing solutions of organic compounds with simultaneous reduction of the salt content and without large drops in current efficiency is achieved. This advantageous result was not to be expected, since desalination of the diluate was expected to take place only to a very small extent, if at all, at the high salt concentration in the concentrate. Surprisingly, however, the high salt concentration of the concentrate did not have the expected adverse influence on the desalination effect. Thus, the salt concentration of the concentrate can be more than twice as high as that necessary for optimum perm selectivity. It can even be more than 100 times higer than the salt concentrations achieved in the diluate by the process. Just as surprising is the fact that even when the solutions used have high contents or organic compounds, eg. solutions having concentrations of more than 10% or even more than 30%, significant losses of the organic compound are not observed. It is also surprising that even aqueous solutions of organic compounds having molecular weights of less than 200 can advantageously be concentrated, and that where solutions which contain highly ionic organic compounds having molecular weights greater than 200 are used the amount of substance lost is only very small. Furthermore, it was not at all possible to foresee that the extent of concentration achieved would be so substantially greater than that expected when water is removed by the standard electroosmosis procedure.

The electrodialysis according to the invention is superior to, for example, ultrafiltration, even for the desalination and concentration of solutions of fairly high molecular weight compounds. It is particularly important where it is intended to reduce the salt content of a product having a high salt content to a very low level. For example, a 30% strength aqueous solution of polymer A having a salt content (NaCl) of 15% can be brought to a content of 60% of A and 7.5% of NaCl in one passes by ultrafiltration. In this procedure (in the ideal case) 50% of the starting solution passes into the permeate in the form of a 15% strength NaCl solution. By subsequent dilution with water to the former volume and further ultrafiltration, the salt content falls further by a half, ie. to 3.75%. The process has to be carried out 5 times in total in order to achieve a residual salt content of <0.5% (degree of desalination ≧95%). The same effect can be achieved in one pass using the novel electrodialysis according to the invention. The novel process therefore also constitutes an economical alternative to ultrafiltration when salts too are to be separated off.

In the novel process, it is also possible to dispense with high current efficiencies and utilize some of the direct current energy to facilitate isolation of the desired product. While in most cases it is sufficient to concentrate the solution by a factor of from 1.2 to 2 and to reduce the salt content of the solution, it may be of interest, for example where the desired product is to be isolated as a dry substance, to concentrate the solution further still, for example by as much as a factor of >3. Although this procedure frequently does not result in a further reduction in the salt content of the solution, the salt content relative to the desired product is reduced further. Another particular advantage of this embodiment of the invention is that evaporation capacity is saved. This increases the flexibility of the process and exposes sensitive products to less heat. Particularly where operation involves fairly small charges, the novel procedure also leads to a reduction in energy costs. This particular embodiment of the process utilizes the surprising effect of the novel process, whereby the amount of water removed is greater than that removed by standard electroosmosis.

The process according to the invention also extends the range of uses of the conventional electrodialysis process, in which is is often technically difficult to process starting solutions which, because of a high salt content, contain precipitates (salting-out effect) or are highly viscous. The starting solution can first be diluted, the novel electrodialysis can be carried out and the solution can then be concentrated to the desired starting concentration. In this way, blockage of the cell and coating of the membranes are avoided, and a high desalination rate in the cell is ensured by using an adequate current. In general, undesirable polarization phenomena (these fared pH shifts in the diluate and concentrate lead to premature destruction of the membranes) are also suppressed by the procedure according to the invention.

In the Examples, percentages are by weight. Concentration factor is the quotient of the weight of the diluate used and the weight of the diluate obtained, while degree of desalination is the quotient of the weight of salt in the diluate used and that in the diluate obtained.

The drawing is a single FIGURE providing a schematic or diagrammatic representation of an electrodialysis cell as used in the following Examples.

EXAMPLE 1

(a) Apparatus:

The electrodialysis cell, which is shown diagrammatically in the Figure, is connected via polyethylene hoses to three separate cycles which supply the cell with the concentrate (1), the diluate (2) and the electrolyte (3) from stock vessels. The cell possesses two platinum electrodes (4), each of 0.35 $dm^2$. The electrode compartments (5) are separated from the adjacent concentrate compartments (6) by cation exchange membranes (7) which are commercially available under the name ®Nafion. Six concentrate compartments (6) and five diluate compartments (8) arranged alternately are located between the electrode compartments. The compartments are separated from One another alternately by cation exchange membranes (9), which are commercially available under the name ®Selemion CMV and anion exchange membranes (10), which are commercially available under the name ®Selemion AMV. The membranes have an active area of 0.37 $dm^2$ and are fastened by means of PVC frames in such a way that they are 2 mm apart. The feed and discharge arrangements to which the cycles are connected are also mounted on the frames. Each of the three cycles is provided with a magnetic centrifugal pump and a heat exchanger. The apparatus is provided with a direct current supply, means for measuring temperature, pH and conductivity and means for flushing with nitrogen.

(b) Carrying out the electrodialyses:

The three cycles of the apparatus are charged with the following solutions:

Electrolyte: 1100 g of 5% strength aqueous $Na_2SO_4$ solution

Concentrate: 4000 g of saturated aqueous NaCl solution containing NaCl as sediment Diluate: 1500 g of a 5% strength aqueous solution of the dye of the formula

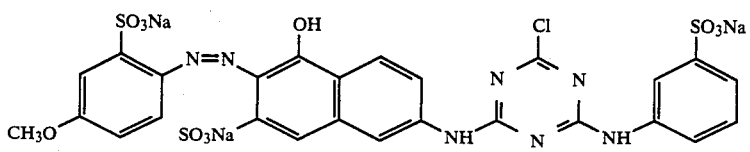

(Molecular weight: 803.5)

The dye solution had a chloride content of 0.58%.

The electrodialysis was carried out at 30° C. and a terminal voltage of 25 V, the solutions being circulated. The initial current of about 1.2 A decreased gradually in the course of desalination, which was monitored analytically (Cl⁻ determination). The electrodialysis was terminated after 18 hours. The diluate obtained was a concentrated aqueous dye solution having a chloride content of 0.11%. The following result was achieved:

| | |
|---|---|
| Concentration factor (diluate): | 1.88 |
| Degree of desalination (diluate): | about 89% |
| Current efficiency: | 10.6% |
| Yield of material: | >99%. |

EXAMPLE 2

(Comparative example)

Electrodialysis was carried out as described in Example 1, except that 1000 g of a 0.5% strength NaCl solution were used as the concentrate, and 1500 g of a 10% strength aqueous solution of the dye, having a chloride content of 0.31%, were used as the diluate. The diluate obtained was a substantially salt-free dye solution which had, however, undergone virtually no concentration. The following result was achieved:

| | |
|---|---|
| Concentration factor: | 1.04 |
| Degree of desalination: | >99% |
| Current efficiency: | about 46% |
| Yield of material: | >99%. |

EXAMPLE 3

1500 g of a 5% strength aqueous solution of the dye of the formula

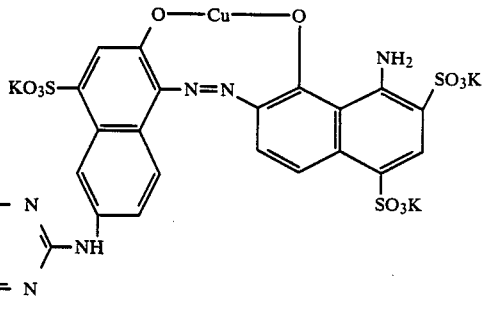

(Molecular weight: 888)

having a chloride content of 0.55% were subjected to electrodialysis by a method similar to that described in Example 1, except that 4000 g of a saturated aqueous potassium chloride solution containing KCL as sediment were used as the concentrate. The electrodialysis was terminated after 43 hours. A concentrated aqueous dye solution having a chloride content of 0.56% was obtained. Result:

| | |
|---|---|
| Concentration factor: | 7.5 |
| Degree of desalination: | about 86% |
| Current efficiency: | about 4% |
| Yield of material: | >99%. |

EXAMPLE 4

The three cycles of the apparatus used in Example 1 were charged with the following solutions:

Diluate: 1500 g of a 10% strength aqueous solution of the dye of the formula

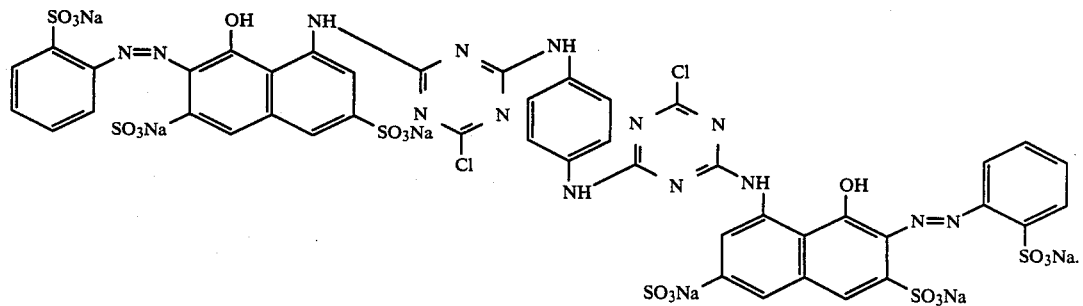

(Molecular weight: 1469)

The dye had a chloride content (NaCL, KCl) of 1.99%.

Concentrate: 4000 g of saturated, aqueous NaCl solution containing sediment

Electrolyte: 1000 g of a 5% strength aqueous Na₂SO₄ solution.

Electrodialysis was started at a cell voltage of 25 V and an initial current of 1.6 A. After an operating time of 27 hours, the current was 0.52 A, and electrodialysis was terminated. The amount of diluate had decreased to 456.9 g, and the chloride content of the diluate was 0.24%. The dye content had increased to about 30%. Result:

| | |
|---|---|
| Concentration factor: | 3.28 |
| Degree of desalination: | 96% |
| Current efficiency: | 25% |
| Yield of material: | >99% |

EXAMPLE 5

The three cycles of the apparatus described in Example 1 were charged with the following solutions:
Diluate: 2000 g of an aqueous sarkosine solution which contained 2.8 moles/kg of sarkosine (molecular weight: 89) and had a chloride content (NaCl) of 9.78%
Concentrate: 2000 g of an aqueous NaCl solution saturated at 25° C.
Electrolyte: 1500 g of a 5% strength aqueous Na2SO4 solution.

Electrodialysis was carried out for 30 hours at a cell voltage of $\leq 30$ V and a current of $>2$ A, the concentrate being changed every 3 hours. At the end, the amount of diluate had decreased to 1100 g, and the diluate had a sarkosine content of 4.20 moles/kg and a chloride content of 0.02%. Result:

| | |
|---|---|
| Concentration factor: | 1.82 |
| Degree of desalination: | >99% |
| Current efficiency: | 60% |
| Yield of material: | 83%. |

EXAMPLE 6

The three cycles of the apparatus described in Example 1 were charged with the following solutions:
Diluate: 2000 g of an aqueous γ-aminobutyric acid solution containing 2.38 moles/kg of γ-aminobutyric acid (molecular weight 103) and having a chloride content (NaCl) of 8.61%.
Concentrate: 2000 g of an aqueous NaCl solution saturated at 25° C.
Electrolyte: 1500 g of a 5% strength aqueous Na2SO4 solution.

Electrodialysis was carried out for 18 hours at a cell voltage of $\leq 20$ V and a current of $\leq 2$ A, the concentrate being changed every 3 hours. At the end, the amount of diluate had decreased to 1233 g, and the diluate had a γ-aminobutyric acid content of 3.62 moles/kg and a chloride content of 0.02%. Result:

| | |
|---|---|
| Concentration factor: | 1.62 |
| Degree of desalination: | >99% |
| Current efficiency: | 68% |
| Yield of material: | 94%. |

EXAMPLE 7

The three cycles of the apparatus described in Example 1 were charged with the following solutions:

Diluate: 2000 g of a 5.75% strength aqueous arbinose solution having a chloride content (NaCl) of 7.02 %
Concentrate: 2500 g of a saturated aqueous NaCl solution
Electrolyte: 1500 g of a 5% strength aqueous Na2SO4 solution.

Electrodialysis was carried out for 15 hours at a cell voltage of $<34$ V and a current of $<2$ A, the concentrate being changed every 3 hours. At the end, the amount of diluate had decreased to 996 g, and the diluate had an arabinose content of 10.49% and a chloride content of 0.01%. Result:

| | |
|---|---|
| Concentration factor: | 2.01 |
| Degree of desalination: | >99% |
| Current efficiency: | 77% |
| Yield of material: | 91%. |

EXAMPLE 8

(Comparative example)

Electrodialysis was carried out as described in Example 7, except that 2000 g of a 5.94% strength aqueous arabinose solution having a chloride content (NaCl) of 7.02% were used as the diluate, and a 0.5% strength aqueous NaCl solution was used as the concentrate. In this case too, the concentrate was changed every 3 hours. (In industrial plants, the concentrate is, as a rule, discharged continuously through an overflow and made up with water in order to prevent the salt concentration of the concentrate from differing too greatly from that of the diluate.) At the end, the final concentration of chloride in the concentrate was 0.38%. The amount of diluate had decreased to 1344 g, and the diluate had an arabinose content of 8.17% and a chloride content of 0.014%. Result:

| | |
|---|---|
| Concentration factor: | 1.49 |
| Degree of desalination: | >99% |
| Current efficiency: | 89% |
| Yield of material: | 92%. |

Comparison with Example 7 shows that, with the same experimental time, a virtually identical yield of material and a slightly poorer current efficiency are obtained, whereas a 35% higher concentration factor is achieved in Example 7.

EXAMPLE 9

The apparatus used was similar to that described in Example 1 and had 20 concentrate compartments instead of 6, and 19 diluate compartments instead of 5. The active membrane and electrode surfaces were each 2 dm². The cation exchange membranes used were the membranes commercially available under the name ®Neosepta CH-45 T, and the anion exchange membranes employed were ®Neosepta ACH-45 T. Three cycles were charged with the following solutions:
Diluate: 9985 g of an aqueous γ-aminobutyric acid solution having a γ-aminobutyric acid content of 0.49 moles/kg and a sulfate content (Na2SO4) of 8.4%
Concentrate: 3992 g of a 15% strength aqueous Na2SO4 solution.

Electrodialysis was carried out for 6.5 hours at a cell voltage of $\leq 30$ V and a current of $\leq 6$ A. At the end, the amount of diluate had decreased to 5461 g, the content of aminobutyric acid had increased to 0.70 mole/kg, and the sulfate content was 0.7%. Result:

| Concentration factor: | 1.83 |
|---|---|
| Degree of desalination: | 95% |
| Current efficiency: | 86% |
| Yield of material: | 79%. |

EXAMPLE 10

The three cycles of the apparatus used in Example 1 were charged with the following solutions:
Diluate: 1500 g of a 5% strength aqueous polydimethyldiallylammonium chloride solution having an NaCl content of 2%
Concentrate: 3000 g of a saturated aqueous NaCl solution containing NaCl as sediment
Electrolyte: 1000 g of a 5% strength aqueous $Na_2SO_4$ solution.

In the course of 27.5 hours at 20° C., a cell voltage of 25 V and an initial current of 1.13 A, the amount of diluate was decreased to 704 g and the NaCl concentration was substantially reduced. Result:

| Concentration factor: | 2.13 |
|---|---|
| Degree of desalination: | 97.1% |
| Current efficiency: | 16.7% |
| Yield of material: | 98.3%. |

EXAMPLE 11

The three cycles of the apparatus used in Example 1 were charged with the following solutions:
Diluate: 1500 g of a 5% strength aqueous polydimethyldiallylammonium chloride solution having an NaCl content of 2%
Concentrate: 300 g of a saturated aqueous NaCl solution containing NaCl as sediment
Electrolyte: 1000 g of a 5% strength aqueous $Na_2SO_4$ solution.

In the course of 16 hours at 60° C., a cell voltage of 25 V and an initial current of 2 A, the amount of diluate decreased to 315 g while the NaCl concentration was substantially reduced. Result:

| Concentration factor: | 4.75 |
|---|---|
| Degree of desalination: | 97.4% |
| Current efficiency: | 13.0% |
| Yield of material: | 95.7%. |

We claim:
1. In a process for concentrating an aqueous solution of an organic compound which contains a salt, with simultaneous reduction of the salt content of this solution, the improvement which comprises:
   subjecting the salt-containing aqueous solution of the organic compound as the diluate to electrodialysis, using a concentrate of an aqueous salt solution which is greater than 1 molar.
2. A process as claimed in claim 1, wherein the concentrate used is an aqueous alkali metal sulfate solution which is greater than 1 molar.
3. A process as claimed in claim 1, wherein the concentrate used is an aqueous alkali metal chloride or bromide solution which is not less than 3 molar.
4. A process as claimed in claim 1, wherein the concentrate used is a salt solution which is saturated at room temperature.
5. A process as claimed in claim 1, wherein the salt used for the concentrate is a water-soluble halide, sulfide, sulfite, sulfate, carbonate, formate or acetate.
6. A process as claimed in claim 1, wherein the salt used for the concentrate is LiCl, KCl, NaCl, $NH_4Cl$, $Li_2SO_4$, $K_2SO_4$ or $Na_2SO_4$.
7. A process as claimed in claim 1, wherein electrodialysis is carried out at no higher than 80° C.
8. A process as claimed in claim 1, wherein the organic compound is electrically neutral and has a molecular weight of not less than about 60.
9. A process as claimed in claim 1, wherein the organic compound is an ionic substance and has a molecular weight of not less than about 120.
10. A process as claimed in claim 1, wherein the organic compound is an ionic monomeric organic compound having a molecular weight of from 200 to 2,000.
11. A process as claimed in claim 1, wherein the organic compound is a water-soluble oligomer or polymer having a molecular weight of from 2,000 to 2 million.
12. A process as claimed in claim 1, wherein the aqueous solution contains not more than 50% by weight of the organic compound and has a salt content of not more than 30% by weight.
13. A process as claimed in claim 1, wherein the electrodialysis is carried out at a temperature of not more than 100° C., using a current density of 10 to 0.01 $A/dm^2$ and a cell voltage of from 0.5 to 2V per subcell, each subcell consisting of a diluate chamber and a concentrate chamber.
14. A process as claimed in claim 13, wherein the current density used is from 5 to 0.05 $A/dm^2$.
15. A process as claimed in claim 13 wherein the electrodialysis is carried out at a temperature of from 15° to 80° C.
16. A process as claimed in claim 14 wherein the electrodialysis is carried out at a temperature of from 15° to 80° C.

* * * * *